United States Patent [19]
Kiaei et al.

[11] Patent Number: 5,710,006
[45] Date of Patent: Jan. 20, 1998

[54] REAGENTS FOR SPECIFIC BINDING ASSAYS

[75] Inventors: David Kiaei, Stoughton; Laurie A. Livshin; Uri Piran, both of Sharon, all of Mass.

[73] Assignee: Chiron Diagnostics Corporation, E. Walpole, Mass.

[21] Appl. No.: 821,664

[22] Filed: Mar. 19, 1997

Related U.S. Application Data

[62] Division of Ser. No. 339,870, Nov. 15, 1994, Pat. No. 5,639,626.

[51] Int. Cl.$^6$ .............................. C12Q 1/68; G01N 33/53; G01N 33/00
[52] U.S. Cl. .............................. 435/6; 435/7.1; 435/7.92; 435/7.93; 435/7.94; 435/7.95; 436/72; 436/175; 536/22.1
[58] Field of Search .............................. 435/7.92, 7.94, 435/7.95, 7.93, 7.1, 6; 436/175, 72; 536/22.1

[56] References Cited

U.S. PATENT DOCUMENTS

| | | | |
|---|---|---|---|
| 4,281,061 | 7/1981 | Zuk et al. | 435/7 |
| 4,668,639 | 5/1987 | Johannsson | 436/518 |
| 4,810,630 | 3/1989 | Craig et al. | 435/7 |
| 4,927,769 | 5/1990 | Chang et al. | 436/518 |
| 4,971,904 | 11/1990 | Luddy | 435/7 |
| 5,248,620 | 9/1993 | Sluka et al. | 436/531 |

OTHER PUBLICATIONS

Haycock, John W., 208 Analytical Biochemistry, 397–399 (1993).

Kenna, J. G. et al., 85 J. Immunological Methods, 409–419 (1985).

Mohammad, Kamaruzaman et al., 117 J. Immunological Methods 141–145 (1989).

OSI Specialties, SILWET® Surfactants (Dec. 9, 1986).

Papavassiliou, Athanasios G. et al., 20 Nucleic Acids Research, 4365–4366 (1992).

Reeves, Stuart G. et al. 26 (7) Analytical Letters 1461–1476 (1993).

Weeks, Ian et al., 29/8 Clin. Chem. 1474–1479 (1983).

*Primary Examiner*—James C. Housel
*Assistant Examiner*—Jennifer Shaver
*Attorney, Agent, or Firm*—Arthur S. Morgenstern; Robert P. Blackburn

[57] ABSTRACT

A sensitive assay method has been discovered that reduces the amount of non-specific binding present in an assay, the method comprising detecting an analyte present in a sample through a specific binding reaction in which either an analogue of the analyte or a specific binding partner of the analyte is immobilized on a solid-phase and said specific binding reaction produces a detectable product immobilized on said solid-phase that may be correlated to the amount of analyte present in the sample wherein said assay employs an effective amount of a surfactant selected from the group consisting of a polyoxyethylene-alkylether, a polyalkylene oxide-modified polydimethylsiloxane block copolymer, a polyalkylene oxide-modified polymethylsiloxane block copolymer, and mixtures thereof to reduce non-specific binding.

17 Claims, No Drawings

5,710,006

REAGENTS FOR SPECIFIC BINDING ASSAYS

This is a divisional of application Ser. No. 08/339,870 filed on Nov. 15, 1994 now U.S. Pat. No. 5,639,626.

FIELD OF INVENTION

This invention relates to heterogeneous specific binding assays.

BACKGROUND OF THE INVENTION

Biochemical binding assays have been widely utilized in recent years to determine the presence and the concentration of analytes in biological specimens. As known in the art, heterogeneous assays are those in which one of the reactive binding partners is bound to a solid-phase. The various types of heterogeneous assays include, for example, the sandwich method, the indirect method, and the competitive method.

As used herein, "binding partner" is defined to include a specific binding partner to the analyte, an analyte analogue, and the analyte. "Non-specific binding" is defined as non-specific interactions of the binding partners with a solid surface in an assay system.

The non-specific binding often reduces the sensitivity of the heterogeneous assays. The sensitivity of the assay typically refers to the smallest mass of analyte that generates a statistically significant change in the signal generated by the assay when compared to the signal reading obtained in the absence of the analyte. There is a need to develop methods to increase the sensitivity of binding assays (i.e. detect smaller amounts of analyte). Furthermore, a high sensitivity assay is typically capable of an overall higher precision measurement of the analytes.

A number of methods are known for reducing the non-specific binding in heterogeneous assays. For example, proteins such as, bovine serum albumin (BSA), gelatin, and casein, have been added to the assay reagents or preadsorbed on the solid-phase in order to block non-specific adsorption sites. Additionally, the use of various surfactants, often in high concentrations, has been reported in the literature.

While known techniques may assist in reducing some non-specific adsorption, many of the prior art techniques have been associated with interference of the desired specific interaction of the binding partners or lead to the displacement of the specific binding complex formed. Additionally, despite the use of high concentrations of protein and surfactant taught by the literature, a considerable amount of non-specific binding typically still exists in many heterogeneous assays. Alternative means to reducing non-specific binding in heterogeneous assays are needed.

SUMMARY OF INVENTION

The problem noted above has been solved with the discovery of a method for detecting or measuring an analyte in a sample, the method comprising (1) reacting a solid phase having attached thereto the analyte, an analogue of the analyte or a specific binding partner with a labeled analyte, labeled analyte analogue or labeled binding partner through a specific binding reaction to produce a detectable product immobilized on said solid-phase; and (2) correlating the amount of detectable product with the amount of analyte present in said sample, wherein a surfactant selected from the group consisting of a polyoxyethylene-alkylether, a polyalkylene oxide-modified polydimethylsiloxane block copolymer, a polyalkylene oxide-modified polymethylsiloxane block copolymer, or a mixture thereof, is present in an effective amount to reduce non-specific binding at least about several fold as compared with assays not employing said surfactants in said effective amount.

It has been discovered that the presence of relatively small amounts of the above-identified surfactants in one or more reagents of the assay reduces non-specific binding associated with solid-phase binding assay techniques. Further, the invention may be used to reduce non-specific binding of various types of proteins and oligonucleotides to the solid-phase with only minimal interference to the desired specific interaction. The inventive method may be used in sandwich, indirect, direct and competitive assay formats. Also included is a kit for carrying out the invention.

DETAILED DESCRIPTION OF INVENTION

According to the invention, in a specific binding reaction at least one of the binding partners is immobilized on a solid-phase. The solid-phase may be prepared from inorganic and/or organic materials that will maintain their structural integrity when exposed to water or biological fluids and are widely available commercially. Suitable inorganic materials that may be used in preparing the solid-phase include, but are not limited to, siliceous materials, silica, bentonite, wollastonite, cordierite, and nonsiliceous metal oxides (including magnetic substances, such as iron oxides, ferrite, nickel oxides, cobalt oxides, and the like). Suitable organic materials that may be used include, but are not limited to, synthetic polymers (such as, for example, polystyrene and derivatives thereof, acrylic polymers, polymethacrylates, polyolefins, halogen-containing polymers, polyester, polyurethanes, and polyamides), natural polymers (such as, for example, polysaccharides, cellulose, dextran, agarose, polypeptide, and proteins) or paper, and the like. Combinations of the organic materials and inorganic materials described above may also be used in preparing the solid-phase. For example, magnetic particles with polymeric coatings around metal oxide cores (such as those described in U.S. Pat. No. 4,554,088, Whitehead, et al, 1985, hereby incorporated by reference) may be used. The solid-phase may be in a particulate form (varying from a finely divided powder, such as magnetite, to a coarse granular material) or a shaped article (such as a bead, test tube, microtiter plate, cuvette, membrane, film, filter paper, disc, and so on). Although any of the above may be used, more preferably, the solid-phase is an article or particle that comprises a polymeric material (most preferably polystyrene, polypropylene, or mixtures thereof) that is present on at least the surface of said article or particle, including solid-phases made of entirely polymeric material as well as polymer coated (preferably polystyrene) magnetic (preferably iron oxide) particles.

The binding partner immobilized on the solid-phase may be an unlabeled specific binding partner of the analyte of interest, an unlabeled analogue of the analyte of interest, or the analyte of interest. The specific binding partner is defined as a substance capable of pairing with the targeted analyte or analyte analogue through a specific binding reaction. The analyte analogue is defined as a substance that is capable of pairing with the specific binding partner of the targeted analyte through a specific binding reaction. The specific binding reaction product complex refers either to a complex of the targeted analyte-specific binding partner, a complex of the analyte analogue-specific binding partner or a complex of a first binding partner-analyte-second binding partner "sandwich" (where the first and second binding partners may be the same or different). The pairing of the specific binding partner and the targeted analyte (and analyte analogue, if used) may be through any number of reactions, including immunological, chemical, and complementary binding. The binding partner that is immobilized on the solid-phase is referred to herein as the "solid-phase reagent". The specific binding partner that used in the invention may be, for example, an antibody, an antigen, avidin, biotin, thyroxin, a thyroxin-binding globulin, a polysaccharide, a oligonucleotide, a polynucleotide, phosphorylcholine, aminoethyldihydrogen phosphate residues, estrogen, vitamin B-12 intrinsic factor, lectins, binding proteins, and various other proteins, receptors, and peptides, nucleic acids, nucleosides, and mixtures thereof.

The invention may be utilized in detecting and/or measuring a number of analytes, including proteins, peptides, polyamino acids, oligonucleotides, RNA, DNA polysaccrides and so on, through binding assays, immunoassays, and nucleic acid hybridization assays (i.e. gene probe assays). This method is particularly useful in reducing non-specific binding of binding partners in assays that measure and or detect the analytes described above.

Any number of known means may be used to directly detect or indirectly detect the immobilized specific binding complex in the assay. Preferably the assay is carried out with the use of a "tracer reagent", as commonly used in immunoassays and gene probe assays. As used herein, the "tracer reagent" is defined as a labeled analyte, a labeled analyte analogue or a labeled specific binding partner. The label attached to the analyte, analyte analogue or specific binding partner is a substance capable of producing a detectable signal. Any number of substances may be used as the label, including, for example, radioisotopes, luminescent, fluorescent or chemiluminescent materials, enzymes, liposomes, as well as metal and non-metal materials. The label can be attached to the specific binding partner, analyte, or analyte analogue directly (e.g. covalent bonding) or indirectly (e.g. biotin/avidin, DNP/anti-DNP) by known techniques. The immobilized complex may be detected, directly (by, for example, measuring the label on the complex) or indirectly (by, for example, measuring the unreacted label) by any number of methods, depending upon what is employed as the label substance. Preferably the label is a chemiluminescent label (most preferably acridinium ester) or an enzymatic label. Particularly preferred chemiluminescent labels are acridinium esters (AE), such as those described in U.S. Pat. No. 4,918,192 (hereby incorporated by reference) and U.S. Ser. No. 08/035,130 (filed Mar. 19, 1993, by Law et al.), where the measurable signal is a chemiluminescent light emission typically activated by an acid reagent (e.g. $H_2O_2$ in $HNO_3$) followed by a base reagent (e.g. NaOH).

Heterogeneous assays typically require a separation of the solid-phase immobilized specific binding reaction complex from the unreacted tracer reagent. A number of means of separation may be employed, many of which use a liquid solution alone or in combination with other techniques (such as, for example, magnetic separation). When used, the liquid solution is referred herein as a "wash reagent" and is typically an aqueous solution that may contain other constituents known to those skilled in the art, as discussed in more detail hereinafter.

Of the three general classes of surfactants described in the invention, the first class are polyoxyethylene-alkylether nonionic surfactants preferably having the following general structure:

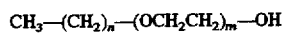

wherein n is an integer having a value of from about 1 to about 18 and m is an integer having a value of from about 2 to about 100. These compounds are widely available commercially. Particularly preferred is polyoxyethylene (4) lauryl ether (BRIJ® 30 surfactant, ICI Americas, Delaware).

The second and third classes of surfactants that may be utilized are polyalkylene oxide-modified polyalkylsiloxane block nonionic copolymers (also commonly referred to as silicone glycol copolymers) of two structural types, identified herein as Formulas A and B. The structural type identified by Formula A are linear polydimethylsiloxanes to which polyethers have been grafted through a hydrosilation reaction. This process results in an alkyl-pendant copolymer in which the polyalkylene oxide groups are attached along the siloxane backbone through a series of hydrolytically stable Si—C bonds. These products are shown by Formula A as follows:

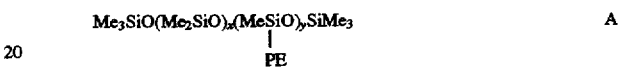

wherein PE=—$CH_2CH_2CH_2O(EO)_o(PO)_p$ Z, Si represents silicon, Me represents methyl, EO represents ethyleneoxy, PO represents 1,2-propyleneoxy, and Z can be either hydrogen or a lower alkyl $C_1$-$C_4$ radical, o is an integer from about 4 to 600, and p is an integer from about 4 to 100, and x and y are integers having a value of from about 1 to about 10. The polyalkylene oxide-modified polydimethylsiloxane copolymers represented by Formula B, below, are branched polydimethylsiloxanes to which polyethers have been attached through condensation chemistry. This process results in an alkoxy-endblocked copolymer in which the polyalkylene oxide groups are attached at the ends of the silicone backbone through Si—O—C bonds. These products are shown by Formula B as follows:

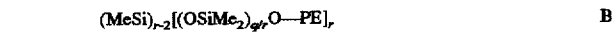

wherein PE=—$(EO)_s(PO)_tR$, R is a $C_1$-$C_4$ lower alkyl group, r and q are integers from about 3 to about 50, s is an integer from about 5 to 100, t is an integer from about 5 to about 100, and Me, Si, EO, and PO are as defined previously. Both classes of these block polymers are not usually present as single chemical compounds but rather are a mixture of several individual compounds each having a different molecular weight and a different molar ratio of polyethylene oxide groups (EO) to polypropylene oxide groups (PO), thus the values for o and p and s and t are average values which can be determined for the mixture from the molecular weight and the molar ratio of EO/PO. Additionally the values of x and y and r and q are also average values that may be determined by the molecular weight of the copolymers. Both classes of block copolymers are widely commercially available such as those manufactured by OSi Specialties under the SILWET® L surfactants series, with SILWET® L-7604 surfactant (polyalkylene oxide modified polydimethyl siloxane) and SILWET® L-7607 surfactant (polyalkylene oxide modified polymethyl siloxane) most preferred.

The usual constituents known to those skilled in the art may be included in the reagent mixtures (i.e. tracer, solid-phase, and wash reagents). Constituents may include buffer substances such as phosphate buffer, citrate buffer, borate buffer and/or bovine serum albumin and/or preservatives and the like. Particularly preferred in tracer reagents and wash reagents is a phosphate buffer and bovine serum albumin.

The identified surfactants may be utilized in different (or all) of the defined reagent mixtures (i.e. solid-phase, tracer, and/or wash reagents) to reduce non-specific binding associated with heterogeneous assays. Any number of combinations may be practiced. When employed in the solid-phase reagent, the surfactant may be included in a solution used to pretreat the solid-phase prior to the attachment of the binding partner to the solid-phase and/or included in the solid-phase reagent after the binding partner is attached to the solid-phase.

Surprisingly, the selected surfactants reduce non-specific binding with minimal to no interruption of the specific binding reaction and specific binding complex on the solid-phase, even when the surfactant is present in the wash reagent. An "effective amount" of the surfactant(s) is defined as an amount of about 0.001 weight/volume percent to about 3 weight/volume percent, with weight/volume (w/v) percentages based on the total volume of each reagent mixture that includes the selected surfactants. This invention is not limited to utilizing the above-stated amount of surfactant(s). A larger amount of the surfactant may be employed, however, one of the advantages of the invention is that the selected surfactants have been found to be effective in reducing non-specific binding when present in relatively small amounts. More preferably the surfactant is employed in a range from 0.005 w/v percent (most preferably 0.01 w/v percent) to 1.5 w/v percent (most preferably 1 w/v percent). The presence of the surfactants in one or more of the solid-phase, tracer, and/or wash reagent(s) in an effective amount may reduce non-specific binding interactions of the binding partners to the solid-phase in an amount of at least about several fold up (in some instances up to 10,000 fold and more) as compared to the non-specific binding of assays not employing said surfactants. In particularly preferred assays, a reduction of non-specific binding of at least about 1000 fold may be accomplished by including at least one of the defined surfactants to one or more of the tracer, solid-phase, or wash reagent(s).

The invention also includes test kits for immunoassays and gene probe assays comprising (a) a solid-phase reagent; (b) a tracer reagent; and (c) a wash reagent, wherein at least one of said reagents includes a surfactant selected from the group consisting of a polyoxyethylene-alkylether, a polyalkylene oxide-modified polymethylsiloxane block copolymer, a polyalkylene oxide-modified polydimethylsiloxane block copolymer, and mixtures thereof, wherein said surfactant is present in an amount ranging from about 0.001 w/v % to about 3 w/v %. Optionally, the test kits may include calibrator solutions which contain a known amount of analyte, as are well known. When the surfactant is employed in the solid-phase reagent, the surfactant may be used to pretreat the solid-phase prior to the attachment of the binding partner to the solid-phase and/or included in the actual reagent mixture after the binding partner has been attached to the solid-phase.

The invention may be practiced in a number of assay formats, including but not limited to those described below.

Labeled analyte or labeled analyte analogue, competitive format: A heterogeneous specific binding assay for detecting or measuring an analyte in a sample, the assay comprising (1) contacting the sample with (a) a tracer reagent comprising a labeled analyte analogue or labeled analyte; and (b) a solid-phase reagent comprising a solid-phase having attached thereto a specific binding partner to said analyte or analyte analogue, to form an immobilized specific binding reaction product complex comprising said labeled analyte analogue or labeled analyte paired with said immobilized specific binding partner; (2) separating said solid-phase having the immobilized complex thereon from said tracer reagent by a method comprising employing a wash reagent; (3) directly or indirectly detecting said label on said immobilized complex; and (4) correlating said detected label with the presence of said analyte in said sample, wherein said method includes the presence of a surfactant selected from the group consisting of a polyoxyethylene-alkylether, a polyalkylene oxide-modified polydimethylsiloxane block copolymer, a polyalkylene oxide-modified polymethylsiloxane block copolymer, or a mixture thereof in one or more reagents selected from the group consisting of said wash reagent, tracer reagent, or solid-phase reagent, said surfactant present in an effective amount to reduce non-specific binding in said assay at least about several fold.

Labeled specific binding partner, competitive format: A heterogeneous specific binding assay for detecting or measuring an analyte in a sample, the assay comprising (1) contacting the sample with (a) a tracer reagent comprising a labeled specific binding partner of the analyte; and (b) a solid-phase reagent comprising a solid-phase having attached thereto an analyte or an analogue analyte, to form an immobilized specific binding reaction product complex comprising said labeled specific binding partner paired with said immobilized analyte or analogue analyte; (2) separating said solid-phase having the immobilized complex thereon from said tracer reagent by a method comprising employing a wash reagent; (3) directly or indirectly detecting said label on said immobilized complex; and (4) correlating said detected label with the presence of said analyte in said sample, wherein said method includes the presence of a surfactant selected from the group consisting of a polyoxyethylene-alkylether, a polyalkylene oxide-modified polydimethylsiloxane block copolymer, a polyalkylene oxide-modified polymethylsiloxane block copolymer, or a mixture thereof in one or more reagents selected from the group consisting of said wash reagent, tracer reagent, or solid-phase reagent, said surfactant present in an effective amount to reduce non-specific binding in said assay at least about several fold.

Sandwich assay, noncompetitive format: A specific binding sandwich assay for detecting or measuring an analyte in a sample, the assay comprising (1) contacting the sample with (a) a tracer reagent comprising a labeled specific binding partner of the analyte; and (b) a solid-phase reagent comprising a solid-phase having attached thereto an unlabeled specific binding partner to the analyte to form an immobilized specific binding reaction product complex comprising said labeled specific binding partner paired with said analyte paired with said immobilized unlabeled specific binding partner; (2) separating said solid-phase having the immobilized complex thereon from said tracer reagent by a method comprising employing a wash reagent; (3) directly or indirectly detecting said label on said immobilized complex; and (4) correlating said signal with the presence of said analyte in said sample, wherein said method includes the presence of a surfactant selected from the group consisting of a polyoxyethylene-alkylether, a polyalkylene oxide-modified polydimethylsiloxane block copolymer, a polyalkylene oxide-modified polymethylsiloxane block copolymer, or a mixture thereof in one or more reagents selected from the group consisting of said wash reagent, tracer reagent, or solid-phase reagent, said surfactant present in an effective amount to reduce non-specific binding in said assay at least about several fold.

In one preferred aspect of this invention, the assay is carried out utilizing polyalkylene oxide modified polydimethyl siloxane in the tracer reagent and polyoxyethylene lauryl ether or polyalkylene oxide modified polymethyl siloxane in the wash reagent.

Alternatively, the above-described surfactants may be used in assay systems that employ a solid phase, but do not employ a separation step (termed pseudo-homogeneous assays herein). In pseudo-homogeneous assays a method of reducing non-specific binding is provided, the method comprising employing one or more of the above-described surfactant(s) in an effective amount in the assay to reduce non-specific binding at least about several fold. Preferably, the surfactants are present in a solution used in such assays, for example the solution wherein the sample is introduced, or (if used) in the tracer reagent, and/or solid phase reagent (if used as a separate reagent).

It is to be understood that various modifications to the invention will be apparent to and can readily be made by those skilled in the art, given the disclosure herein, without departing from the scope and materials of this invention. It is noted that the following examples given herein are intended to illustrate and not to limit the invention thereto.

EXAMPLES

Materials that were used in the Examples included BRIJ® 30 surfactant [polyoxyethylene (4) lauryl ether]; TWEEN® 20 surfactant (polyoxyethylene sorbitan monolaurate), polyethylene oxide (PEO, Cat. No. P 6667, average MW 10,000) and PVA (polyvinyl alcohol, Cat. No. P 8136, average MW 30,000-70,000), bovine gamma globulin (BgG), and hemoglobulin (HB), all of which were all purchased from Sigma Chemical Co. (St. Louis, Mo.). SILWET® L-7604 (polyalkylene oxide modified polydimethyl siloxane) and SILWET L-7607 (polyalkylene oxide modified polymethyl siloxane) were obtained from OSi Specialties, Inc. TRITON® X-100 and TRITON X-705 surfactants (octyl phenol polyether alcohols) were obtained from Union Carbide Corp. PLURONIC® poly(oxyethylene-oxypropylene) copolymer surfactants and TETRONIC® alkoxylated diamine surfactants were obtained from BASF Corp. (Parsippany, N.J.). Polystyrene tubes, 12×75 mm, were purchased from Sarstedt Inc. (Cat. No. 55.476, Pennsauken, N.J.). Polypropylene cuvettes, 12×75 mm, were obtained from Becton Dickinson Corp. (Falcon 2002, Lincoln Park, N.J.). Polypropylene cuvettes were manufactured for Ciba-Corning Diagnostics Corp. (Medfield, Mass.). Polystyrene-encapsulated magnetic particles were purchased from Bangs Laboratories, Inc. (Stock No. M0009400CN, Carmel, Ind.). The monoclonal antibodies against triiodothyronine, creatine kinase, dinitrophenol, and thyroid stimulating hormone were mouse antibodies prepared with techniques well-known to those skilled in the art. The acridinium ester (AE) label was conjugated to the various specific binding partners (thus forming the tracer) in a manner as described in I. Weeks, et al., "Acridinium Esters as High-Specific Activity Labels in Immunoassay", Clin. Chem., 29, 1474–1479 (1983). All weight/volume percentages of the surfactants are based on the total volume of each reagent mixture that includes the surfactant. The AE-labeled oligonucleotide was a 5'-$NH_2$-mecA-495 where the sequence was 5' GAA GAT GGT ATG TGG AAG TTA GAT ATT, where A=adenine, G=guanine, and T=thymine.

A magnetic separation rack (available from Ciba Corning Diagnostics Corp., Medfield, Mass.) was used in the separation step. The chemiluminescent labels were activated by first contacting the separated solid-phase with 0.3 ml of Flash Reagent 1 (0.1N $HNO_3$ in a 0.5% aqueous solution of $H_2O_2$) followed by contacting the solid-phase with 0.3 ml of Flash Reagent 2 [0.25N NaOH in a 0.5% aqueous solution of ARQUAD® 16–50 N-alkyl trimethyl ammonium chloride (50% active purchased from AKZO Chemical Inc., Chicago, Ill.)].

Example 1

Effect of BRIJ 30 and SILWET L-7607 in the Wash Reagent on Non-Specific Binding of Bovine Gamma Globulin (BgG) to Polystyrene Tube In the first step, the following reagents were added to a 12×75 mm polystyrene tube: (a) 0.1 ml of PBS/BSA buffer [0.05M sodium phosphate monobasic, 0.15M sodium chloride, 1 mM ethylenediaminetetraacetic acid (EDTA), 0.02 w/v % sodium azide, 0.1 w/v % bovine serum albumin (BSA), pH 7.4]; (b) 0.1 ml of acridinium ester (AE)-labeled bovine gamma globulin (BgG) at approximately $1 \times 10^8$ RLU (relative light unit) in PBS/BSA buffer; and (c) 0.5 ml of PBS/BSA. After each addition, the tube was vortexed.

In the second step, following 1 hour of incubation at room temperature, the content of each tube was decanted and blotted on an absorbent tissue paper for 3 min. Next, a wash solution (1 ml PSA/BSA buffer) was prepared without a surfactant (CONTROL) as well as numerous wash reagents that included 1 ml of PBS/BSA buffer with 0.1 w/v % of the different surfactants shown in TABLE I. Each reagent was added to separate tubes, vortexed, decanted and blotted for 3 min. This wash step was repeated for a total of 4 times. Thereafter, 5 ml of deionized water were added to each tube, decanted, and blotted for 3 min. Lastly, 0.1 ml of deionized water was added to each tube and the non-specific binding of AE-labeled BgG to the polystyrene tube was measured after flashing the AE label by adding 0.3 ml of Flash Reagent 1 followed by 0.3 ml of Flash Reagent 2 whereupon the resulting light emission was measured by a Magic® Lite Analyzer II (Ciba Corning Diagnostics Corp., Medfield, Mass.). Data measured from each test tube are summarized in TABLE 1. The data shown are presented as fractional non-specific binding defined as Relative Light Units (RLUs) remaining in each tube divided by the input RLU, i.e. $1 \times 10^8$.

TABLE 1

| Non-Specific Binding of Acridinium Ester (AE)-Bovine Gamma Globulin (BgG) on Polystyrene Tube | | |
|---|---|---|
| Surfactant in PSA/BSA Wash Reagent | Amount of Surfactant | Fractional Non-Specific Binding |
| None (Control) | 0 | $4 \times 10^{-4}$ |
| BRIJ ® 30[1] (Invention) | 0.1 w/v % | $3 \times 10^{-8}$ |
| SILWET ® L-7607[2] (Invention) | 0.1 w/v % | $3 \times 10^{-8}$ |
| TWEEN ® 20[3] (Comparative) | 0.1 w/v % | $2 \times 10^{-6}$ |
| TRITON ® X-100[4] (Comparative) | 0.1 w/v % | $2 \times 10^{-7}$ |

[1] Polyoxyethylene (4) lauryl ether
[2] Polyalkyleneoxide modified polymethyl siloxane
[3] Polyoxyethylene sorbitan monolaurate
[4] octyl phenol polyether alcohol As the results in TABLE 1 show, addition of 0.1 w/v % BRIJ 30 or 0.1 w/v % SILWET L-7607 to the PBS/BSA wash reagent was observed to reduce fractional non-specific binding of AE-BgG to polystyrene tubes more than 10,000 fold. In contrast, addition of 0.1 w/v % of TWEEN 20 or TRITON X-100 to the wash solution was observed to reduce non-specific binding 200 and 2000 fold, respectively.

Example 2

Effect of BRIJ 30 and SILWET L-7607 in the Wash Reagent on Non-Specific Binding of Anti-Thyroid Stimulating Hormone (TSH) Antibody to Polystyrene

Non-specific binding of a mouse monoclonal antibody against thyroid stimulating hormone (TSH) to polystyrene tube was measured as described in Example 1, with the exception that anti-TSH was substituted for the BgG and the first step utilized a BSA solution of 0.1 ml of 5 w/v % BSA solution (0.05M sodium phosphate monobasic, 0.02 w/v % sodium azide, 5 w/v % BSA, pH 7.4) instead of the PSA/BSA buffer.

TABLE 2

Non-Specific Binding of AE-Monoclonal Antibody (Anti-TSH) to Polystyrene Tube

| Surfactant in PBS/BSA Wash Reagent | Amount of Surfactant | Fractional Non-Specific Binding |
|---|---|---|
| None (Control) | 0 | $5.5 \times 10^{-4}$ |
| BRIJ ® 30 (Invention) | 0.1 w/v % | $1 \times 10^{-8}$ |
| SILWET ® L-7607 (Invention) | 0.1 w/v % | $1 \times 10^{-8}$ |
| TRITON ® X-705 (Comparative) | 0.1 w/v % | $1.2 \times 10^{-5}$ |

As demonstrated in TABLE 2, addition of 0.1 w/v % BRIJ 30 or SILWET L-7607 to the wash reagent was observed to reduce fractional non-specific binding of Anti-TSH to polystyrene over 50,000 fold. In contrast, addition of 0.1 w/v % TRITON X-705 to the wash solution (such as taught by U.S. Pat. No. 4,668,639) was observed to reduce the fractional non-specific binding less than 50 fold.

Example 3

Effect of Concentration of BRIJ 30 and SILWET L-7607 in the Wash Reagent on Non-Specific Binding of Various Tracer Reagents

AE-labeled proteins BgG and hemoglobin (HB) as well as monoclonal antibodies against triiodothyronine, creatine kinase (CK-MB), dinitrophenol, and Thyroid stimulating hormone (TSH) were tracer reagents evaluated for non-specific binding to polystyrene using two different concentrations of various surfactants in the PBS/BSA buffer with the protocol described in Example 2, with the exception that in the second step the tubes were washed three times instead of four. The concentration and types of surfactants tested are shown in TABLES 3 and 4, where the following is a list of abbreviations used: AE=acridinium ester label; BgG=bovine gamma globulin; HB=hemoglobin, Anti-TY 1–3=three different lines of anti-triiodothyronine antibodies, Anti-CK= anti-creatine kinase antibody, Anti-DNP=anti-dinitrophenol antibody, and Anti-TSH=anti-thyroid stimulating hormone antibody; E=times $10^x$ (i.e. 7.7E-8=$7.7 \times 10^{-8}$); Inv.= invention; Comp.=comparison; and SILWET=a polyalkylene oxide modified polymethyl siloxane (SILWET L-7607).

TABLE 3

Effect of BRIJ 30 and Triton X100 on Fractional Non-Specific Binding

| | | Wash Reagent PBS/BSA | | | |
|---|---|---|---|---|---|
| AE-labeled Tracer | Control | BRIJ-30 0.01 w/v % (Inv.) | TRITON X100 0.01 w/v % (Comp.) | BRIJ-30 0.1 w/v % (Inv.) | TRITON X100 0.1 w/v % (Comp.) |
| BgG | 5.4E-5 | 1.2E-6 | 5.7E-6 | 7.7E-8 | 8.4E-7 |
| HB | 6.9E-4 | 3.1E-6 | 6.3E-5 | 1.4E-6 | 1.1E-6 |
| Anti-TY1 | 6.5E-6 | 7.7E-8 | 2.8E-7 | <5E-8 | 1.1E-7 |
| Anti-TY2 | 2.1E-5 | 1.5E-7 | 3.1E-6 | <5E-8 | 3.1E-7 |
| Anti-TY3 | 4.2E-5 | 2.4E-7 | 2.7E-6 | 1.1E-7 | 5.5E-7 |
| Anti-CK | 1.4E-5 | 2.3E-7 | 3.1E-6 | 1.9E-7 | 5.0E-7 |
| Anti-DNP | 7.9E-6 | 3.3E-7 | 8.3E-7 | <5E-8 | <5E-8 |
| Anti-TSH | 5.5E-4 | 1.7E-6 | 1.1E-5 | 3.4E-7 | 1.2E-6 |

TABLE 4

Effect of SILWET L-7607 and TWEEN 20 on Fractional Non-Specific Binding

| AE-labeled Tracer | Control | Wash Reagent PBS/BSA | | | |
|---|---|---|---|---|---|
| | | SILWET 0.01 w/v % (Inv.) | TWEEN-20 0.01 w/v % (Comp.) | SILWET 0.1 w/v % (Inv.) | TWEEN-20 0.1 w/v % (Comp.) |
| BgG | 4.3E-5 | 2.2E-6 | 1.8E-6 | 3.1E-7 | 7.2E-7 |
| HB | 6.2E-4 | 3.2E-5 | 2.1E-4 | 8.2E-7 | 9.8E-6 |
| Anti-TY1 | 6.1E-6 | 2.6E-7 | 3.1E-7 | 1.1E-7 | 4.8E-8 |
| Anti-TY2 | 2.1E-5 | 1.8E-6 | 2.3E-6 | <5E-8 | 1.1E-6 |
| Anti-TY3 | 3.5E-5 | 2.6E-6 | 4.7E-6 | 3.8E-7 | 1.5E-6 |
| Anti-CK | 1.3E-5 | 3.8E-6 | 1.9E-6 | 3.3E-7 | 7.7E-7 |
| Anti-DNP | 7.3E-6 | 1.8E-7 | 4.3E-7 | <5E-8 | 1.4E-7 |
| Anti-TSH | 5.4E-4 | 7.9E-6 | 1.1E-5 | 5.8E-7 | 3.8E-6 |

As the results summarized in TABLES 3 and 4 illustrate, the average decrease in the non-specific binding of these eight tracers with 0.01 w/v % BRIJ 30 was observed as approximately 150 fold and SILWET L-7607 was approximately 40 fold, compared to 20 and 15 fold reduction obtained with TWEEN 20 and TRITON X-100, respectively. At 0.1 w/v %, the average decrease in non-specific binding for BRIJ 30 was observed as 850 fold. At 0.1 w/v % SILWET L-7607 showed an average decrease in non-specific binding of 602 fold. At 0.1 w/v %, the comparative surfactants, TRITON X-100 and TWEEN 20, showed a 273 and 63 fold, respectively.

Example 4

Effect of Surfactants in Tracer Reagent on Non-Specific Binding of Anti-Creatine Kinase Antibody to Polystyrene Non-specific binding of an AE-labeled anti-creatine kinase monoclonal antibody to polystyrene tube was measured with the protocol described in Example 2 with several modifications. AE-labeled creatine kinase antibody was tested for the non-specific binding and the surfactants tested (as identified in TABLE 5) were added to the tracer reagent in Step 1 rather than the wash reagent in Step 2. Additionally, the surfactants were employed at a higher concentration, 1 w/v %. Results are summarized in TABLE 5.

TABLE 5

Fractional Non-Specific Binding of AE-Anti-Creatine Kinase Antibody to Polystyrene Tube

| Surfactant in PSA/BSA Tracer Reagent | Amount of Surfactant | Fractional Non-Specific Binding |
|---|---|---|
| Control | 0 | $3.1 \times 10^{-5}$ |
| SILWET ® L-7604[1] (Invention) | 1 w/v % | $1.4 \times 10^{-7}$ |
| TETRONIC ® 904[2] (Comparative) | 1 w/v % | $2.2 \times 10^{-6}$ |
| TRITON ® X-705[3] (Comparative) | 1 w/v % | $8.6 \times 10^{-6}$ |

[1] Polyalkyleneoxide modified polydimethyl siloxane
[2] Alkoxylated ethylene diamine
[3] Octylphenoxy polyethoxy ethanol As shown by the data in TABLE 5, the addition of 1 w/v % SILWET L-7604 was observed to reduce non-specific binding of the Anti-Creatine Kinase antibody to polystyrene 200 fold. Addition of 1 w/v % TETRONIC 904 to PBS/BSA resulted in a 10 fold reduction. Addition of 1 w/v % Triton® X-705 was observed to decrease non-specific binding by four fold.

Example 5

Effect of Surfactants in Tracer Reagent on Non-Specific Binding of BgG to Polystyrene Non-specific binding of a AE-labeled BgG to polystyrene tube was measured as described in Example 4 with the modifications that the AE-BgG was substituted in the tracer reagent. Results are summarized in TABLE 6.

TABLE 6

Non-specific Binding of Acridinium Ester (AE)-BgG Polystyrene Tube

| Surfactant in PSA/BSA Tracer Reagent | Amount of Surfactant | Fractional Non-Specific Binding |
|---|---|---|
| Control | 0 | $3.5 \times 10^{-4}$ |
| SILWET ® L-7604[1] (Invention) | 1 w/v % | $4.6 \times 10^{-6}$ |
| TETRONIC ® 904[2] (Comparison) | 1 w/v % | $2.7 \times 10^{-6}$ |
| PLURONIC ® P84[3] (Comparison) | 1 w/v % | $5.3 \times 10^{-6}$ |

[1] Polyalkyleneoxide modified polydimethyl siloxane
[2] Alkoxylated ethylene diamine
[3] Poly(oxyethylene-oxypropylene) copolymer

Example 6

Effect of Surfactants in Wash Reagent on Non-Specific Binding of BgG to Polypropylene Fractional non-specific binding of AE-BgG to the polypropylene cuvettes was studied as follows: 0.1 ml of 5 w/v % BSA solution described in Example 2 was added to each cuvette. Next, 0.1 ml of AE-BgG at $1 \times 10^8$ RLU and 0.5 ml of PBS/BSA buffer were added sequentially. After one hour of incubation at room temperature, cuvettes were washed three times with either water ("Control") or a wash reagent comprising PBS buffer (0.05M sodium phosphate monobasic, 0.15M sodium chloride, 1 mM EDTA, and 0.02 w/v % sodium azide), 1 w/v % polyvinyl alcohol (PVA), and 0.1 w/v % BRIJ 30 ("PBS/PVA/BRIJ 30") and thereafter flashed with Flash Reagent 1 and Flash Reagent 2 and measured. The RLUs remaining in each cuvette was determined on the ACS:180® instrument (a fully automated, random access, chemiluminescent immunoassay system, as manufactured by Ciba Corning Diagnostics Corp.). The measured RLUs remaining in each cuvette represented the fractional non-specific binding, where the fractional non-specific binding of BgG to polypropylene cuvettes was observed to be reduced from $1.6 \times 10^{-4}$ to $7.8 \times 10^{-7}$ when the water wash was replaced with PBS/PVA/BRIJ 30 wash reagent.

Example 7

Effect of BRIJ 30 in the Wash Reagent on Specific and Non-Specific Binding of Creatine Kinase (CK-MB) Assay Effect of wash reagent composition on specific and non-specific binding of Magic® Lite CK-MB (creatine kinase) assay was studied. 0.1 ml of CK-MB standard, containing either zero or 51.6 ng/ml CK-MB, was added to each polystyrene tube followed by 0.1 ml of AE-labeled anti-CK-MB antibody ($1.6 \times 10^7$ RLU). Next, 0.5 ml of anti-CK-BB antibody immobilized on paramagnetic iron oxide particles was added. Following one hour of incubation, each tube was washed two times with water; PBS/BSA; or PBS/BSA/0.1 w/v % BRIJ 30 and thereafter flashed and measured in the manner described in Example 1. Results are summarized in TABLE 7 below. As shown, addition of BRIJ 30 to the wash reagent improved the signal-to-noise of the assay from 263 to 417.

TABLE 7

| | Specific and Non-Specific Binding of Creatine Kinase Assay | | |
|---|---|---|---|
| | Creatine Kinase Concentration (ng/ml) | | |
| Wash Reagent | 0 | 51.6 | Signal/Noise |
| Water (Control) | 1933 | 302240 | 156 |
| PBS/BSA (Control) | 860 | 226235 | 263 |
| PBS/BSA/BRIJ 30 (Invention) | 557 | 232125 | 417 |

Example 8

Effect of Surfactant in Wash Reagent on Non-Specific Binding of an Oligonucleotide to Polystyrene Fractional non-specific binding of AE-labeled oligonucleotide 5'-NH$_2$-mecA-495 to polystyrene tubes was significantly reduced by addition of 0.1 w/v % BRIJ 30 to the wash reagent. The protocol of Example 2 was used with three washes using either water or PBS/PVA/BRIJ 30. Non-specific binding of the oligonucleotide tracer to polystyrene was reduced from $1.4 \times 10^{-4}$ to $<5 \times 10^{-8}$ when the standard washing solution, water, was replaced with PBS/PVA/BRIJ 30.

Example 9

Effect of Surfactant in Wash Reagent on Non-Specific Binding of an Oligonucleotide to Polypropylene Fractional non-specific binding of AE-labeled oligonucleotide 5'-NH$_2$-mecA-495 to polypropylene tubes was reduced from $5.9 \times 10^{-4}$ to $1.9 \times 10^{-5}$ when the water wash solution was replaced with a PBS/PVA/BRIJ 30. The modification of the protocol of Example 2 as described in Example 6 was followed.

Example 10

Effect of Surfactant in Wash Reagent on Non-Specific Binding of an Oligonucleotide to Polypropylene The non-specific binding of the AE-labeled oligonucleotide tracer 5'- NH$_2$-mecA-495 to polypropylene cuvettes was evaluated using TETRONIC 904 surfactant. The assay protocol was as follows: First, 0.1 ml of 5 w/v % BSA was added to each cuvette followed by 0.1 ml of the 5'-AE-NH$_2$-495 in PBS/BSA with or without 0.1 w/v % TETRONIC 904. Next, 0.45 ml of PBS/BSA with or without 0.1 w/v % TETRONIC 904 was introduced into each cuvette. After 7.5 min of incubation at 37° C., the cuvettes were washed 3 times with PBS/0.1 w/v % BRIJ 30. The non-specific binding of the oligonucleotide to the polypropylene cuvettes was reduced from $1.4 \times 10^{-5}$ to $5.2 \times 10^{-6}$ when 0.1 w/v % TETRONIC 904 was added to the buffer solutions as flashed and measured in the manner described in Example 6.

Example 11

Effect of Surfactants in Wash or Solid-Phase Reagent on Non-Specific Binding of BgG to Polystyrene-Coated Magnetic Particles In this experiment, the effect of BRIJ 30 and TETRONIC 908 on non-specific binding of AE-BgG to polystyrene encapsulated magnetic particles was studied. First, 0.1 ml of PBS/BSA or PBS containing 1 w/v % TETRONIC 908 was added to a polystyrene tube. Then, 0.5 ml of magnetic particles at 0.1 mg/ml in PBS/BSA was added followed by 0.1 ml of AE-BgG at $10^8$ RLU. The samples were vortexed following each addition. After one hour incubation at room temperature, samples were washed three times with PBS/BSA or PBS/PVA/BRIJ 30 and thereafter flashed and measured in the manner described in Example 1. Results are summarized in TABLE 8.

TABLE 8

| | Fractional Non-Specific Binding of AE-Labeled BgG to Magnetic Polystyrene Microspheres | |
|---|---|---|
| | FRACTIONAL NON-SPECIFIC BINDING Solid-phase Reagent: | |
| Wash Reagent | PBS/BSA | PBS/1% TETRONIC 908 |
| PBS/BSA (Control) | $3 \times 10^{-4}$ | $1 \times 10^{-4}$ |
| PBS/PVA/BRIJ 30 (Invention) | $7 \times 10^{-5}$ | $3 \times 10^{-5}$ |

Example 12

Effect of Various Surfactants Added to the Solid-Phase Reagent on Non-Specific Binding of BgG to Polystyrene-Coated Magnetic Particles The protocol for this study has been described in Example 11. The wash solution for all samples of this study was PBS/PVA/BRIJ 30. Results are summarized in TABLE 9.

TABLE 9

Fractional Non-Specific Binding of AE-Labeled BgG to Magnetic Polystyrene Microspheres

| Surfactant in PBS/PVA Wash Reagent | Surfactant/Polymer in PBS Buffered Solid-phase Reagent | Fractional Non-Specific Binding |
|---|---|---|
| 0.1 wt. % BRIJ 30 | None | $9.6 \times 10^{-5}$ |
| 0.1 wt. % BRIJ 30 | 1 w/v % TWEEN 20 | $1.9 \times 10^{-4}$ |
| 0.1 wt. % BRIJ 30 | 1 w/v % TRITON X-100 | $3.3 \times 10^{-4}$ |
| 0.1 wt. % BRIJ 30 | 1 w/v % PLURONIC F108 | $4.0 \times 10^{-5}$ |
| 0.1 wt. % BRIJ 30 | 1 w/v % TETRONIC 908 | $3.5 \times 10^{-5}$ |
| 0.1 wt. % BRIJ 30 | 1 w/v % PEO | $8.8 \times 10^{-5}$ |
| 0.1 wt. % BRIJ 30 | 1 w/v % PVA | $4.7 \times 10^{-5}$ |

It is not intended that the scope of the claims appended hereinafter are limited to the description as set forth herein, but rather that the claims be construed as encompassing all features of patentable novelty which reside in the present invention, including all features which would be treated as equivalents thereof by those skilled in the art to which the invention pertains.

That which is claimed is:

1. A heterogeneous specific binding assay for detecting or measuring an analyte in a sample, the assay comprising:
    (1) contacting the sample with (a) a tracer reagent comprising a labeled analyte analogue or a labeled analyte; and (b) a solid-phase reagent comprising a solid-phase having attached thereto a specific binding partner to said analyte or analyte analogue, to form an immobilized specific binding reaction product complex comprising said labeled analyte analogue or said labeled analyte paired with said immobilized specific binding partner;
    (2) separating said solid-phase having the immobilized complex thereon from said tracer by a method comprising employing a wash reagent;
    (3) directly or indirectly detecting said label on said immobilized complex; and
    (4) correlating said detected label with the presence of said analyte in said sample,
    wherein said method includes the presence of a surfactant selected from the group consisting of a polyalkylene oxide-modified polydimethylsiloxane block copolymer, a polyalkylene oxide-modified polymethylsiloxane block copolymer, or a mixture thereof, said surfactant present in an effective amount to reduce non-specific binding in said assay wherein said specific binding partner is an oligonucleotide.

2. An assay according to claim 1 wherein said surfactant is used to pretreat the solid-phase prior to the attachment of the specific binding partner.

3. An assay according to claim 1 wherein said surfactant is present in in step (1).

4. An assay according to claim 1 wherein said surfactant is a polyalkylene oxide modified polymethylsiloxane block copolymer.

5. An assay according to claim 1 further comprising polyoxyethylene lauryl ether in said wash reagent.

6. An assay according to claim 1 wherein said non-specific binding is reduced at least about 1000 fold as compared with an assay having no surfactant present.

7. A heterogeneous specific binding assay for detecting or measuring an analyte in a sample, the assay comprising:
    (1) contacting the sample with (a) a tracer reagent comprising a labeled specific binding partner of the analyte; and (b) a solid-phase reagent comprising a solid-phase having attached thereto an analyte or an analogue analyte, to form an immobilized specific binding reaction product complex comprising said labeled specific binding partner paired with said immobilized analyte or analogue analyte;
    (2) separating said solid-phase having the immobilized complex thereon from said tracer reagent by a method comprising employing a wash reagent;
    (3) directly or indirectly detecting said label on said immobilized complex; and
    (4) correlating said detected label with the presence of said analyte in said sample, wherein said assay includes the presence of a surfactant selected from the group consisting of a polyalkylene oxide-modified polydimethylsiloxane block copolymer, a polyalkylene oxide-modified polymethylsiloxane block copolymer, or a mixture thereof in one or more reagents selected from the group consisting of said wash reagent, tracer reagent, or solid-phase reagent, said surfactant present in an effective amount to reduce non-specific binding wherein said specific binding partner is an oligonucleotide.

8. An assay according to claim 7 wherein said surfactant is used to pretreat the solid-phase prior to the attachment of the specific binding partner.

9. An assay according to claim 8 wherein said surfactant is present during said step (1).

10. An assay according to claim 9 wherein said surfactant is present in a wash reagent mixture.

11. An assay according to claim 7 wherein said assay further comprises employing a polyoxyethylene lauryl ether in said wash reagent.

12. An assay according to claim 11 wherein said non-specific binding is reduced at least about 1000 fold as compared with an assay having no surfactant present.

13. A specific binding sandwich assay for detecting or measuring an analyte in a sample, the assay comprising:
    (1) contacting the sample with (a) a tracer reagent comprising a labeled specific binding partner of the analyte; and (b) a solid-phase reagent comprising a solid-phase having attached thereto an unlabeled specific binding partner to the analyte to form an immobilized specific binding reaction product complex comprising said labeled specific binding partner paired with said analyte paired with said immobilized unlabeled specific binding partner;
    (2) separating said solid-phase having the immobilized complex thereon from said tracer reagent by a method comprising employing a wash reagent;
    (3) directly or indirectly detecting said label on said immobilized complex; and
    (4) correlating said signal with the presence of said analyte in said sample, wherein said method includes the presence of a surfactant selected from the group consisting of a polyalkylene oxide-modified polydimethylsiloxane block copolymer, a polyalkylene oxide-modified polymethylsiloxane block copolymer, or a mixture thereof said surfactant present in an effective amount to reduce non-specific binding in said assay at least about several fold wherein said specific binding partner is an oligonucleotide.

14. An assay according to claim 13 wherein said surfactant is used to pretreat the solid-phase prior to the attachment of the specific binding partner.

15. An assay according to claim 13 wherein said surfactant is present during said step (1).

16. An assay according to claim 13 wherein said assay further comprises employing a polyoxyethylene lauryl ether in said wash reagent.

17. An assay according to claim 13 wherein said non-specific binding is reduced at least about 1000 fold as compared with an assay having no surfactant present.

* * * * *